United States Patent [19]

Branstetter et al.

[11] Patent Number: 5,007,423
[45] Date of Patent: Apr. 16, 1991

[54] OXIMETER SENSOR TEMPERATURE CONTROL

[75] Inventors: Ronald L. Branstetter; Jonathan P. Jaeb; Jeffrey M. Gabelmann, all of San Antonio, Tex.

[73] Assignee: Nippon Colin Company Ltd., Japan

[21] Appl. No.: 417,209

[22] Filed: Oct. 4, 1989

[51] Int. Cl.$^5$ ............................................. A61B 5/00
[52] U.S. Cl. .................................................. 128/633
[58] Field of Search ........................... 128/633; 356/41

[56] References Cited
U.S. PATENT DOCUMENTS
4,890,619  1/1990  Hatschek ............................ 128/633

FOREIGN PATENT DOCUMENTS
247777  12/1987  European Pat. Off. ............ 128/633

Primary Examiner—Max Hindenburg
Assistant Examiner—Kevin Pontius
Attorney, Agent, or Firm—Oliff & Berridge

[57] ABSTRACT

A system for measuring blood oxygen saturation uses a noninvasive optical technique. A patient's arterial blood is illuminated with light at two different wavelengths and the intensity of the reflected light is correlated with an oxygen saturation reference curve to determine the oxygen saturation of the patient's blood. The optical sensor includes one or more controlled heat sources which are used to maintain the patient's tissue at a predetermined temperature. Safety circuits are also provided in order to prevent thermal burns to a patient in the event of a system failure.

19 Claims, 2 Drawing Sheets

OXIMETER SENSOR TEMPERATURE CONTROL

FIELD OF THE INVENTION

The present invention relates generally to monitoring equipment which can be used to estimate the degree of oxygen saturation of arterial blood. More specifically, the present invention provides an improved oximeter sensor comprising heating elements which increase blood flow in the sampled tissue and thereby provide more accurate measurements of the blood oxygen saturation in the tissue.

BACKGROUND OF THE INVENTION

It is well known that hemoglobin and oxyhemoglobin have different optical absorption spectra and that this difference in absorption spectra can be used as a basis for an optical oximeter. Most of the currently available oximeters using optical methods to determine blood oxygen saturation are based on transmission oximetry. These devices operate by transmitting light through an appendage such as a finger or an earlobe. By comparing the characteristics of the light transmitted into one side of the appendage with that detected on the opposite side, it is possible to compute oxygen concentrations. The main disadvantage of transmission oximetry is that it can only be used on portions of the body which are thin enough to allow passage of light. There has been considerable interest in recent years in the development of an oximeter which is capable of using reflected light to measure blood oxygen saturation. A reflectance oximeter would be especially useful for measuring blood oxygen saturation in portions of the patient's body which are not well suited to transmission measurements.

Various methods and apparatus for utilizing the optical properties of blood to measure blood oxygen saturation have been shown in the patent literature. Representative devices for utilizing the transmission method of oximetry have been disclosed in U.S. Pat. Nos. 4,586,513; 4,446,871; 4,407,290; 4,226,554; 4,167,331; and 3,998,550. In addition, reflectance oximetry devices and techniques are shown generally in U.S. Pat. Nos. 4,447,150; 4,086,915; and 3,825,342.

A theoretical discussion of a basis for the design of a reflectance oximeter is contained in "Theory and Development of a Transcutaneous Reflectance Oximeter System for Noninvasive Measurements of Arterial Oxygen Saturation," by Yitzhak Mendelson (Published Doctoral Dissertation), No. 8329355, University Microfilms, Ann Arbor, Mich. (1983). A theoretical discussion of the optical properties of blood is found in "Optical Scattering in Blood," by Narayanan R. Pisharoty, (Published Doctoral Dissertation), No. 7124861, University Microfilms, Ann Arbor, Mich. (1971).

Numerous other works have disclosed theoretical approaches for analyzing the behavior of light in blood and other materials. The following is a brief list of some of these references: "New Contributions to the Optics of Intensely Light-Scattering Materials, Part 1," by Paul Kubelka, Journal of the Optical Society of America, Volume 38, No. 5, May 1948; "Optical Transmission and Reflection by Blood," by R. J. Zdrojkowski and N. R. Pisharoty, IEEE Transactions on Biomedical Engineering, Vol. BME-17, No. 2, April 1970.

One of the difficulties which has been encountered in the use of optical oximeters is inaccuracy of measurements in cool environments which cause the patient's tissue to have reduced blood flow. The reflectance oximeter sensor provided by the present invention overcomes these difficulties, as described in greater detail below.

SUMMARY OF THE INVENTION

The present invention provides a noninvasive reflectance oximeter which is capable of providing accurate indications of a patient's blood oxygen saturation, even in cool environments. In the preferred embodiment of the present invention, the oxygen saturation of a patient's arterial blood is determined by a noninvasive optical technique which takes advantage of differences in the absorption spectra of hemoglobin and oxyhemoglobin.

In its simplest form, the invention comprises an optical sensor including means for illuminating the patient's arterial blood with light at two different wavelengths, means for measuring the intensity of the reflected light after contact with the blood and means for correlating the intensity of the light reflected with an oxygen saturation reference curve to determine the oxygen saturation of the patient's blood. One of the sources of light is at a wavelength for which the absorption coefficients of hemoglobin and oxyhemoglobin differ substantially from one another. The reflected light signal detected by the system comprises an alternating-current (AC) component and a direct-current (DC) component for each of the respective light sources. The components of each of the reflected signals are used to form a voltage amplitude ratio. This ratio is then correlated with an oxygen saturation reference curve to obtain an indication of the oxygen saturation of the patient's arterial blood. The improved sensor provided by the present invention comprises means for heating the tissue beneath the sensor to increase the blood flow therein and, therefore, to allow the sensor to obtain a more accurate indication of the blood oxygen saturation therein. The heat sources for warming the tissue are LEDs essentially the same as those used to illuminate the tissue. These heating LEDs are controlled in a manner to maintain the tissue at a predetermined temperature. Heat sensing means are employed to monitor the temperature of the tissue and to produce an output control signal to control operation of the heating LEDs. Safety circuits are also provided to prevent thermal burns to the patient in the event of an equipment failure.

DETAILED DESCRIPTION OF THE PREFERRED EMBODIMENT

Figure 1:
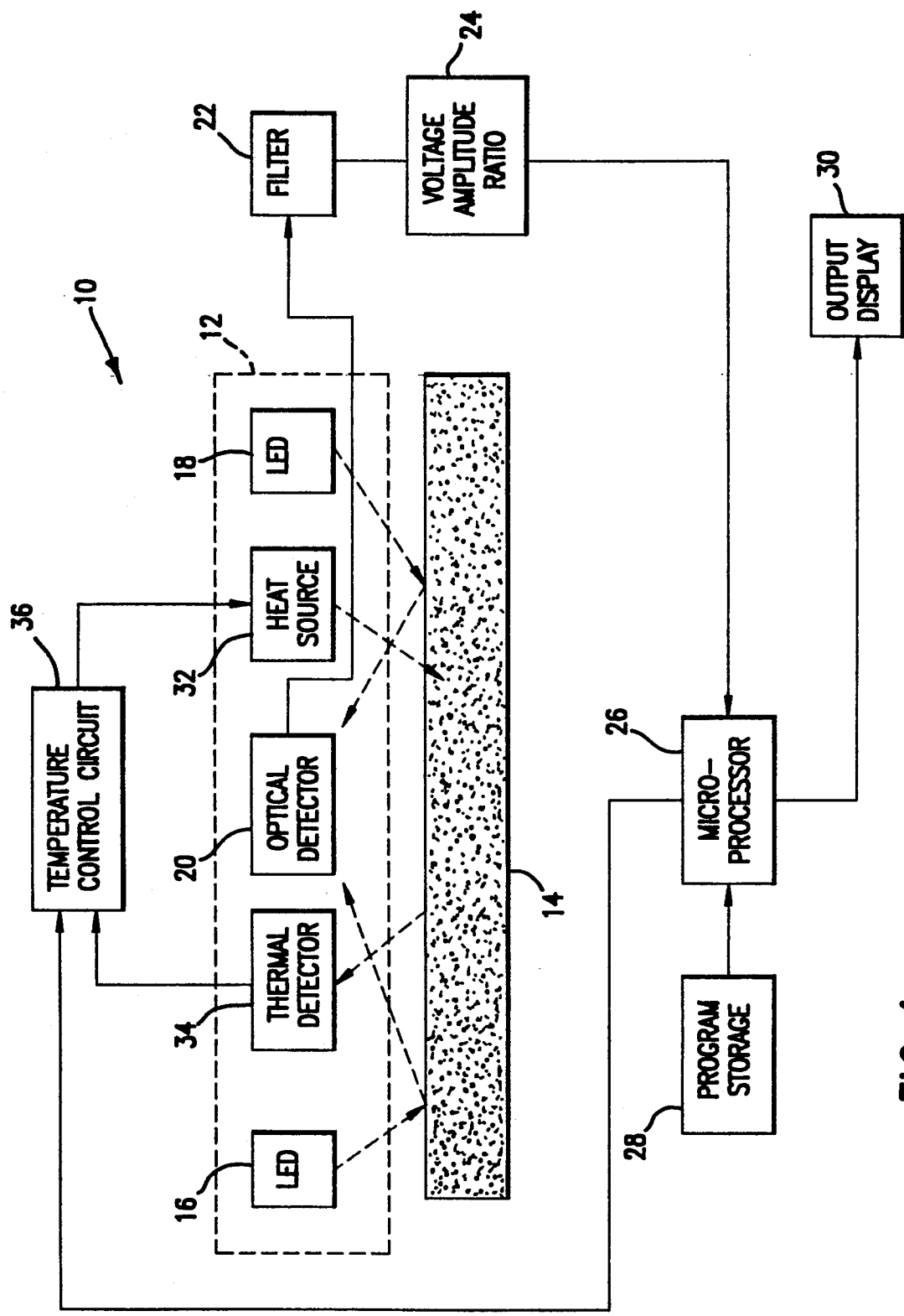
FIG. 1 is a schematic block diagram of a simplified embodiment of the noninvasive blood oxygen saturation monitoring system of the present invention.

Referring to the drawings in more detail, and to FIG. 1 in particular, the noninvasive monitoring system 10 of the present invention is shown in its preferred embodiment. A monitoring probe 12 is positioned over a portion of the patient's tissue 14 such that light produced by two light emitting diodes (LED) 16 and 18 will be reflected by arterial blood in the tissue and detected by a photodetector 20. In the preferred embodiment, the LED 16 emits light having a wavelength of 660 nm (red) and the LED 18 emits light having a wavelength of 900 nm (infrared). However, the invention is not intended to be limited to any specific wavelength of light produced by the above mentioned LEDs. Proper operation of the invention requires only that one of the sources of light have a wavelength at which the absorption coefficients of hemoglobin and oxyhemoglobin differ substantially from one another. The output of the photodetector 20 will be an electrical signal representing a combination of direct-current (DC) and alternating-current (AC) components of the light reflected by the arterial blood in the tissue 14. This output signal is processed by an appropriate filter 22 to produce separate signals corresponding to the AC and DC voltage components of each of the wavelengths of incident light. These AC and DC voltage signals for each wavelength are then processed by a voltage amplitude ratio circuit 24 to provide an output signal corresponding to the ratio of the AC/DC portions of the reflected signals. The AC/DC ratios at each wavelength are then used to form a final composite ratio. The final voltage amplitude ratio output signal is provided to a microprocessor 26 which calculates the oxygen saturation in accordance with an algorithm and a data reference curve stored in program storage 28. The calculated oxygen saturation is then displayed on an appropriate display device 30. Exemplary methods for calculating oxygen saturation are described in U.S. Pat. No. 4,714,080 to Edgar, Jr. et al., and U.S. Pat. No. 4,796,636 to Branstetter et al., the disclosures of both of which are incorporated herein by reference.

As will be discussed in greater detail below, the tissue 14 is maintained at a predetermined temperature by a heat source 32. In the preferred embodiment of the system, the heat source is an infrared LED essentially identical to the infrared light source LED 18, although it is readily apparent that other suitable heat sources can be employed. In another embodiment, the heat source LED also serves as a light source LED. During times in which a reflected light measurement is made, the LED is controlled as a light source. At times when a reflected light measurement is not being made, the LED is controlled as a heat source. Furthermore, it should be noted that although a single heat source 32 is shown in FIG. 1, two or more heat sources can be used to achieve the desired degree of temperature control.

When using LEDs as heat sources, the tissue is heated through two mechanisms. First, power delivered to each LED is converted to heat in the LED by the common resistive heating method. Heat thus generated is conducted from the LED through the sensor and into the skin. Second, power delivered to the LED is converted to light. Because tissue absorbs little light, the light is transmitted and scattered into the capillary bed where it is absorbed by the blood. Upon absorption, heat is generated. This second heating mechanism provides a direct means for the energy from the LED to be transferred to the capillary bed without relying on thermal conduction through the skin.

In the preferred embodiment, the heating LEDs emit light in the infrared spectrum. Infrared light will penetrate deeper into the tissue than visible light. Also, using present technology, infrared LEDs provide more optical power than LEDs emitting visible light.

A thermal sensor 34 is used to monitor the temperature of the tissue 14 and provides a temperature output signal. In the preferred embodiment of the system, a thermistor is used as the thermal sensor. The temperature output signal is provided as an input signal to a temperature control circuit 36 which controls operation of the heat source 32.

The temperature control circuit 36 is a feedback network with an adjustable setpoint. The adjustable setpoint allows the system to select the temperature at which the sensor thermistor will be maintained. In general, it is desirable for the skin underlying the thermal sensor 34 to be maintained at 37° C., which corresponds to normal "core" body temperature. The feedback signal, provided by the thermistor, is converted to a voltage output, amplified, filtered, and compared to an adjustable setpoint voltage which is proportional to the desired temperature. The difference between the setpoint voltage and the thermal sensor 34 voltage, defined as the loop error signal, is amplified and fed into a pulse width modulation (PWM) circuit. This pulse width modulated error signal is used to control the output power of the heating LED's 32.

A thermistor was chosen as the thermal sensor 34 element in the preferred embodiment because they are small, reliable and have a relatively fast response time. The preferred embodiment of the invention uses a Fenwal 8K small bead thermistor. The thermistor's output voltage versus temperature curve is essentially linear for temperature values within the range of 30° to 40° C. This linearity allows the thermistor to be modeled as a straight line approximation in the setpoint control hardware using a $y = mx + b$ format where:

y = setpoint voltage,
m = characteristic curve slope,
x = temperature, and
b = characteristic curve intercept.

Figure 2:
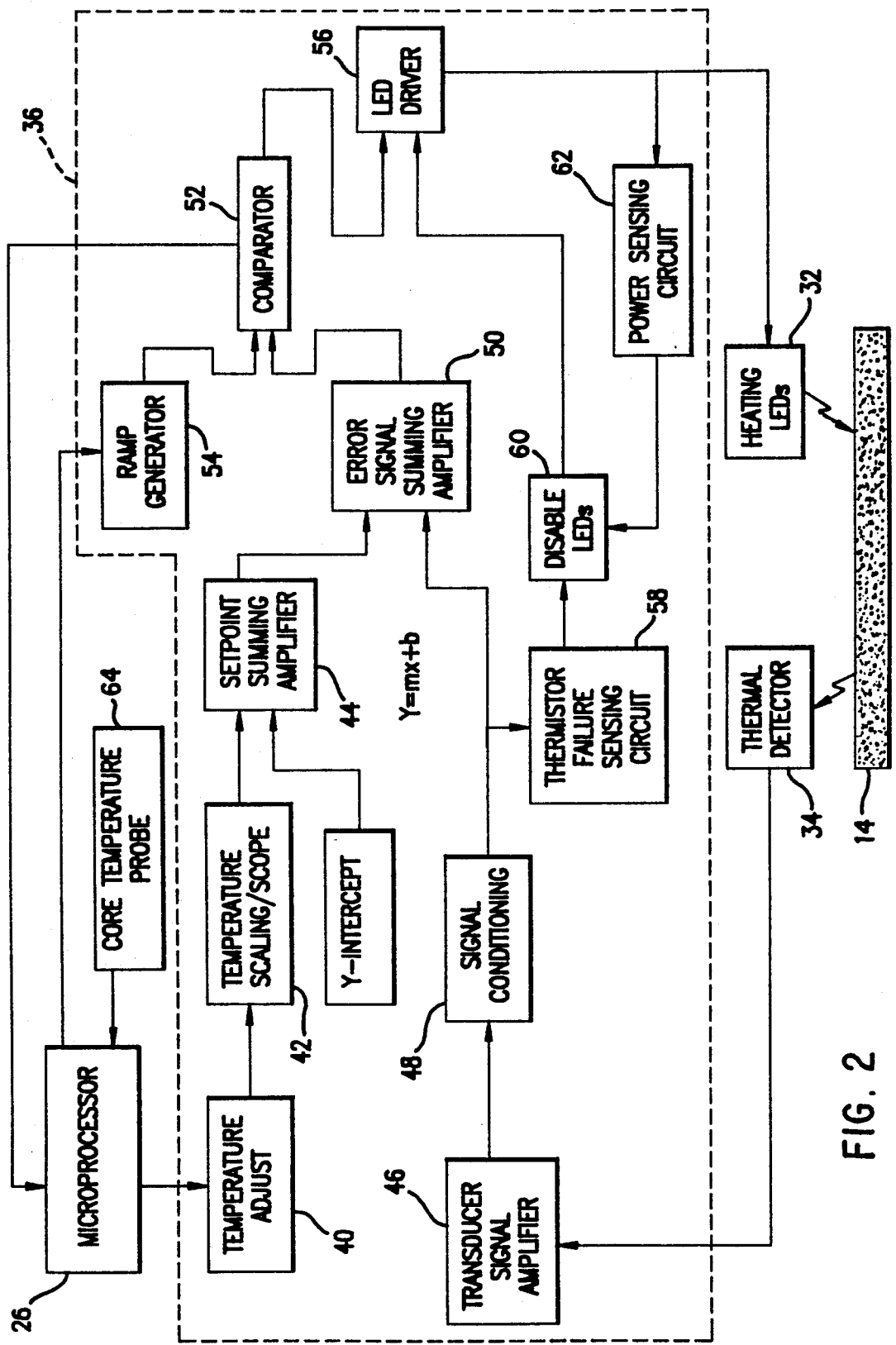
FIG. 2 is a schematic block diagram of a circuit for monitoring the temperature of a patient's tissue and for controlling heating LEDs to maintain the tissue at a predetermined temperature.

Referring to FIG. 2, the functional modules of the temperature control system 36 will be discussed in more detail. The temperature adjust module 40 is an adjustable voltage divider whose output voltage is controlled by the microprocessor 26 to be proportional to the desired setpoint temperature. The desired setpoint temperature is selected by the system operator, or in another embodiment, the desired setpoint temperature may be controlled thermostatically. For example, core temperature probe 64 is used to provide a reference signal to the microprocessor 26 such that the thermal sensor 34 temperature is automatically maintained corresponding to the core body temperature.

The output signal from the temperature adjust module 40 is provided to the temperature scaling/slope module 42 which is an inverting amplifier used to scale the output signal from the temperature adjust module and to set the slope of the $y = mx + b$ curve. The setpoint summing amplifier 44 provides the y-intercept for the straight line approximation model.

The output signal from the thermal sensor 34, e.g., a thermistor is provided to the transducer signal amplifier 46 which amplifies the signal to an appropriate level for processing by the signal conditioning circuit 48. The signal conditioning circuit 48 consists of a two-pole, active low-pass filter whose 3 dB point is 1 Hz. The output of this active filter is routed together with the output of the setpoint summing amplifier 44 to the error signal summing amplifier 50. The error signal summing amplifier 50 adds the amplified and filtered thermal sensor 34 output signal to the inverse of the set point voltage. The difference between those two signals (the loop error signal) is provided to comparator 52 where it is compared to a 2 KHz voltage ramp generated by a timer circuit (the ramp generator circuit 54). When the error signal is greater than the ramp voltage, the output of the comparator activates the LED driver 56. The output of the comparator 52 is a signal whose duty cycle is proportional to the error signal. A large error signal will cause long current pulses to be delivered to the heating LED's 32, thus providing the desired heat to the tissue.

The present invention further includes safety features which, in the event of equipment failure, prevent thermal burns to the patient. The thermal sensor failure sensing circuit 58 is used to sense a failure of thermal sensor 34. This circuit may use a comparator operating in a window configuration to determine whether thermal sensor 34 is open circuited or short circuited as recognized by those skilled in the art. Other circuits are possible. When either of these conditions is present, an output signal is provided which disables the LEDs. When this failure detection circuit 58 detects a failure condition, it will cause the LED disable circuit 60 to disable the LED driver circuit 56.

Power sensing circuit 62 provides a second level of safety. In the preferred embodiment, this circuit monitors the power delivered to the LEDs, and, through the use of analog filters, determines average LED power. If the average LED power exceeds a predetermined undesirable level, the LEDs are disabled by the LED disable circuit 60. In this fashion, power sensing circuit 62 preferably provides a safety shutdown not only for the heating LEDs, but for all the LEDs.

Although the method and apparatus of the present invention has been described in connection with the preferred embodiment, it is not intended to be limited to the specific form set forth herein, but on the contrary, it is intended to cover such alternatives, modifications and equivalents within the spirit and scope of the invention as defined by the appended claims.

What is claimed is:

1. A blood oxygen saturation monitoring system for non-invasive measurement of oxygen saturation of arterial blood in tissue of a patient, comprising:
    a first source of electromagnetic radiation at a first wavelength;
    a second source of electromagnetic radiation at a second wavelength;
    means for positioning said first and second sources of electromagnetic radiation on the patient so as to illuminate a sample of blood in the tissue;
    detecting means for receiving electromagnetic radiation reflected by said sample of blood;
    data processing means for calculating the blood oxygen saturation of said tissue responsive to said detected reflected electromagnetic radiation; and
    means for maintaining said tissue at a predetermined temperature responsive to the temperature of said tissue.

2. The blood oxygen saturation monitoring system according to claim 1, wherein said means for maintaining said tissue at a predetermined temperature comprises a light emitting diode.

3. The blood oxygen monitoring system according to claim 2, wherein said means for maintaining said tissue at a predetermined temperature further comprises a thermal sensor in the form of a thermal sensor, said thermistor providing an output signal indicative of the temperature of said tissue.

4. The blood oxygen monitoring system according to claim 3, wherein said means for maintaining said tissue at a predetermined temperature further comprises a control circuit responsive to said output signal of said thermal sensor, said control circuit comprising a feedback circuit with an adjustable setpoint.

5. The blood oxygen monitoring system according to claim 4, wherein said control circuit further comprises a core temperature probe for monitoring a patient's body temperature to provide a reference signal which indicates the desired setpoint.

6. The blood oxygen monitoring system according to claim 3, further comprising safety means coupled to said means for maintaining for disabling said means for maintaining to thereby; prevent thermal burns to said tissue in the event of a system failure.

7. The blood oxygen monitoring system according to claim 6, wherein said safety means comprises a thermal sensor failure circuit for detecting a failure in the thermal sensor, and means for disabling said light emitting diode when a failure is detected by said thermal sensor failure circuit.

8. The blood oxygen monitoring system according to claim 6, wherein said safety means comprises a power sensing circuit for monitoring the power delivered to said light emitting diode, and means for disabling said light emitting diode if the delivered power exceeds a predetermined value.

9. The blood oxygen monitoring system according to claim 8, wherein said power sensing circuit monitors the average delivered power.

10. The blood oxygen saturation monitoring system of claim 3, wherein said thermal sensor comprises a thermistor.

11. The blood oxygen monitoring system according to claim 1, further comprising safety means coupled to said means for maintaining for disabling said means for maintaining thereby preventing thermal burns to said tissue in the event of a system failure.

12. The blood oxygen saturation monitoring system of claim 1, wherein said predetermined temperature is about 37° C.

13. A blood oxygen saturation monitoring system for noninvasive measuring of arterial blood oxygen saturation in tissue of a patient comprising:
    a first source of electromagnetic radiation at a first wavelength;
    a second source of electromagnetic radiation at a second wavelength;
    means for positioning said first and second sources of electromagnetic radiation on the patient so as to illuminate a sample of blood in tissue;
    detecting means for receiving electromagnetic radiation reflected by said sample of blood;
    data processing means for computing the blood oxygen saturation of said tissue responsive to said detected reflected electromagnetic radiation;
    a light emitting diode producing electromagnetic radiation for heating said tissue;
    means for controlling said light emitting diode thereby maintaining said tissue at a predetermined temperature; and
    safety means for disabling said light emitting diode thereby preventing thermal burns to said tissue in the event of a system failure.

14. The blood oxygen saturation monitoring system of claim 13, wherein said predetermined temperature is about 37° C.

15. A method for determining the oxygen saturation of arterial blood in tissue, comprising the steps of:

illuminating a sample of said blood with electromagnetic radiation at a first wavelength;

illuminating said sample of blood with electromagnetic radiation at a second wavelength;

controlling the temperature of said tissue to maintain said tissue at a predetermined temperature;

collecting electromagnetic radiation reflected by said sample of blood in the tissue at the predetermined temperature and forming data signals therefrom; and processing said data signals to calculate the blood oxygen saturation of the blood in said tissue.

16. The method of claim 15, wherein said controlling step comprises the steps of measuring the temperature of said tissue;

controlling the temperature of said tissue by heating said tissue when said temperature of said tissue is less than said predetermined temperature.

17. A blood oxygen saturation monitoring system for non-invasive measurement of oxygen saturation of arterial blood in tissue of a patient, comprising:

a first source of electromagnetic radiation at a first wavelength;

a second source of electromagnetic radiation at a second wavelength;

means for positioning said first and second sources of electromagnetic radiation on the patient so as to illuminate a sample of blood in the tissue;

detecting means for receiving electromagnetic radiation reflected by said sample of blood;

data processing means for calculating the blood oxygen saturation of said tissue responsive to said detected reflected electromagnetic radiation; and means for maintaining said tissue at a predetermined temperature comprising:

a light emitting diode;

a thermal sensor having an output signal indicative of the temperature of said tissue;

a control circuit responsive to said output signal of said thermal sensor and having a feedback circuit with an adjustable setpoint; and a core temperature probe coupled to said control circuit for monitoring the patient's body temperature and for providing a reference signal for comparison with said setpoint.

18. A blood oxygen saturation monitoring system for noninvasive measurement of oxygen saturation of arterial blood in tissue of a patient, comprising:

a first source of electromagnetic radiation at a first wavelength;

a second source of electromagnetic radiation at a second wavelength;

means for positioning said first and second sources of electromagnetic radiation on the patient so as to illuminate a sample of blood in the tissue;

detecting means for receiving electromagnetic radiation reflected by said sample of blood;

data processing means for calculating the blood oxygen saturation of said tissue responsive to said detected reflected electromagnetic radiation; and means for maintaining said tissue at a predetermined temperature comprising:

a light emitting diode;

a thermal sensor having an output signal indicative of the temperature of said tissue;

safety means coupled to said means for maintaining for disabling said means for maintaining thereby preventing thermal burns to said tissue in the event of a system failure, said safety means further comprising a thermal sensor failure circuit for detecting a failure in said thermal sensor and means for disabling said light emitting diode when said failure is detected.

19. A blood oxygen saturation monitoring system for noninvasive measurement of oxygen saturation of arterial blood in tissue of a patient, comprising:

a first source of electromagnetic radiation at a first wavelength;

a second source of electromagnetic radiation at a second wavelength;

means for positioning said first and second sources of electromagnetic radiation on the patient so as to illuminate a sample of blood in the tissue;

detecting means for receiving electromagnetic radiation reflected by said sample of blood;

data processing means for calculating the blood oxygen saturation of said tissue responsive to said detected reflected electromagnetic radiation; and means for maintaining said tissue at a predetermined temperature comprising:

a light emitting diode;

a thermal sensor having an output signal indicative of the temperature of said tissue;

safety means coupled to said means for maintaining for disabling said means for maintaining thereby preventing thermal burns to said tissue in the event of a system failure, said safety means further comprising a power sensing circuit for monitoring the power delivered to said light emitting diode and means for disabling said light emitting diode if the power delivered exceeds a predetermined value.

* * * * *